United States Patent
Faisandier et al.

(10) Patent No.: US 8,109,793 B2
(45) Date of Patent: Feb. 7, 2012

(54) SELF-CONTAINED ELECTRONIC INSTRUMENT WITH A MICROCONTROLLER, IN PARTICULAR AN AMBULATORY MEDICAL RECORDER

(75) Inventors: Yves Faisandier, Paris (FR); Sylvain Christophle-Boulard, Sainte Genevieve des Bois (FR)

(73) Assignee: ELA Medical S.A.S., Montrouge (FR)

( * ) Notice: Subject to any disclaimer, the term of this patent is extended or adjusted under 35 U.S.C. 154(b) by 1517 days.

(21) Appl. No.: 11/281,345

(22) Filed: Nov. 16, 2005

(65) Prior Publication Data
US 2006/0121755 A1    Jun. 8, 2006

(30) Foreign Application Priority Data
Nov. 17, 2004   (FR) ...................................... 04 12182

(51) Int. Cl.
*H01R 24/00*    (2011.01)
(52) U.S. Cl. .......................... 439/630; 439/660; 600/300
(58) Field of Classification Search .................. 600/300, 600/301; 128/903–905, 920; 439/630, 660
See application file for complete search history.

(56) References Cited

U.S. PATENT DOCUMENTS

| 5,701,894 A | 12/1997 | Cherry et al. |
| 6,386,920 B1 * | 5/2002 | Sun ................................ 439/630 |
| 6,790,178 B1 * | 9/2004 | Mault et al. .................... 600/300 |

FOREIGN PATENT DOCUMENTS

| FR | 2 693 007 A1 | 12/1993 |
| FR | 2 704 677 A1 | 11/1994 |

OTHER PUBLICATIONS

Foreign Search Report (FR).

* cited by examiner

*Primary Examiner* — Henry M Johnson, III
*Assistant Examiner* — Kai Rajan
(74) *Attorney, Agent, or Firm* — Orrick Herrington & Sutcliffe, LLP

(57) ABSTRACT

The instrument includes a connector block (24) suitable for receiving a removable memory card (12), a printed circuit (20), a case including an opening (16) for insertion of the memory card, and contacts (48) for reprogramming the microcontroller (22). The reprogramming contacts (48) are disposed on the printed circuit (20) at a distance from terminals (26) for making contact with the memory card, in the space that the connector block (24) occupies on the printed circuit, and they are available from the inside volume of the connector block. The instrument is essentially lacking in any opening dedicated to accessing the reprogramming contacts, with access to these contacts being possible via the opening in the case and the inside volume of the connector block by inserting an insert (52) into the instrument instead of and replacing a memory card.

15 Claims, 1 Drawing Sheet

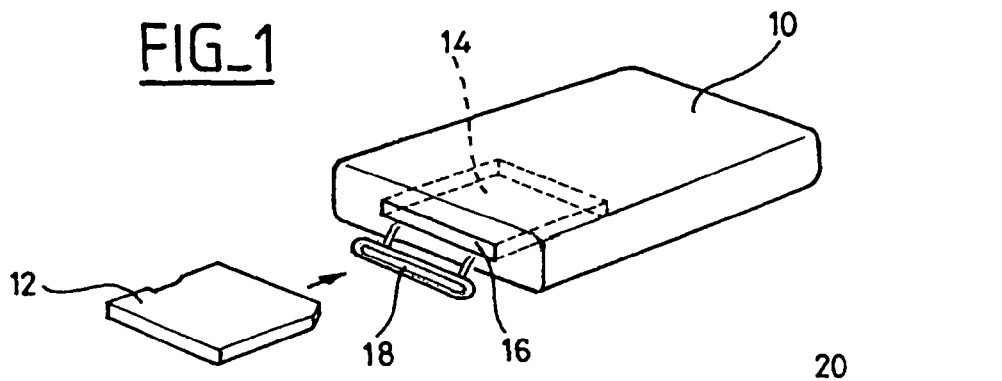
FIG_1
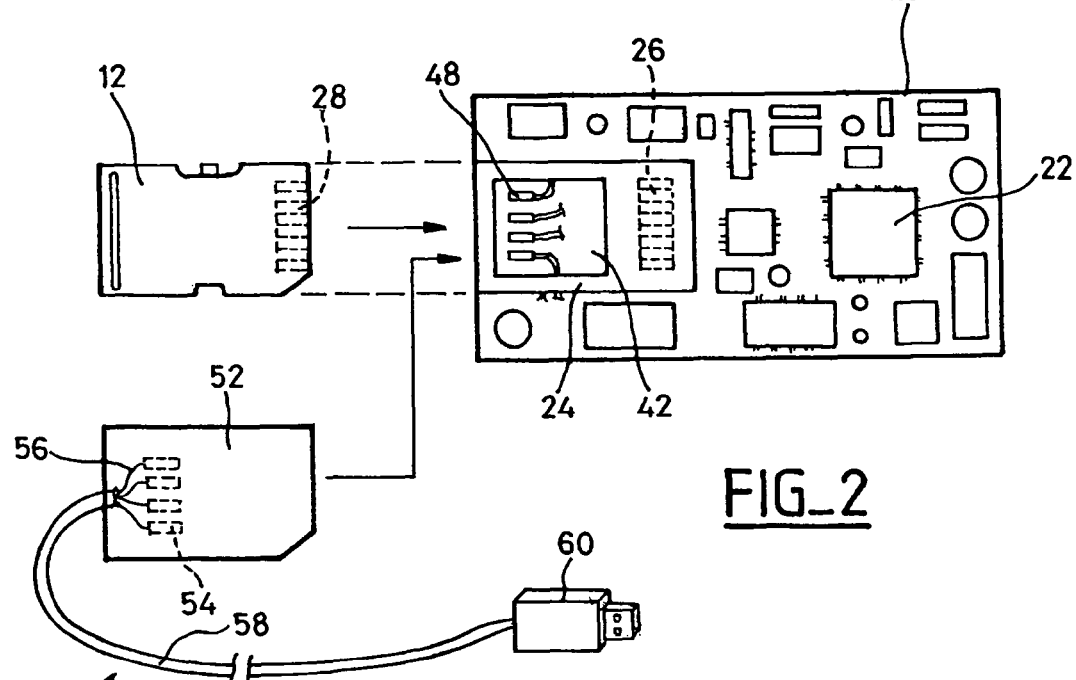
FIG_2
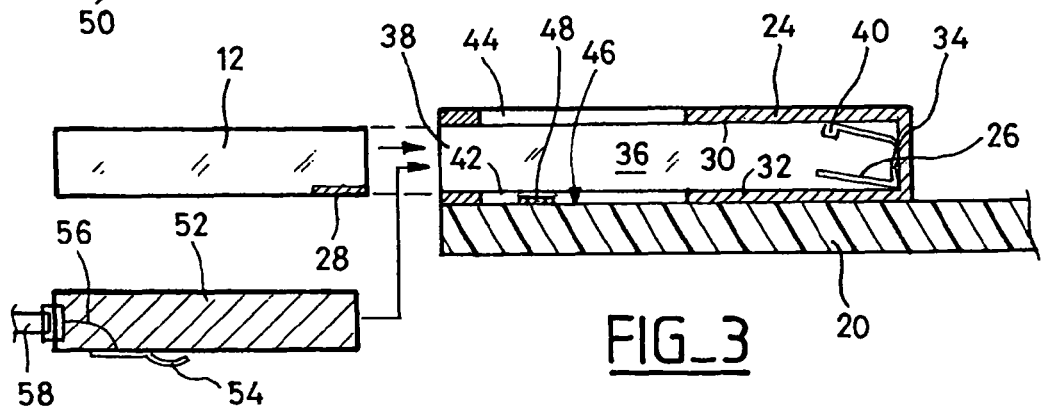
FIG_3

SELF-CONTAINED ELECTRONIC INSTRUMENT WITH A MICROCONTROLLER, IN PARTICULAR AN AMBULATORY MEDICAL RECORDER

FIELD OF THE INVENTION

The invention relates to self-contained electronic instruments that include a microcontroller or a microprocessor, and particularly to medical instruments, such as ambulatory recorders of electrocardiograms, that make it possible over a long period, either continuously or on-demand, to sense and store cardiac activity signals from external electrodes.

However, as will be understood, the invention is not limited to this particular type of instrument, and it can also relate to sensing or recording other physiological data such as breathing rate, blood pressure, etc.

Nor indeed is the invention restricted to medical instruments; it can be applied to numerous other electronic instruments that are controlled by a reprogrammable microcontroller (or microprocessor) making use of a removable memory card for storing a large volume of data: data files, images, sound sequences, etc.

BACKGROUND OF THE INVENTION

For ambulatory electrocardiogram recorders, such instruments are nowadays characterized by a case worn or carried by the patient, e.g., on a belt or in a pocket, and connected to some number of electrodes or other external sensors. The recorder is controlled by a microcontroller, and the data that it senses, either raw or after preprocessing, is typically stored on a large-capacity removable data medium so as to enable data to be recorded in full over a very long period, typically in the range one day to several months.

Nowadays, magnetic recording media (cassettes) have been replaced by electronic memories such as flash memories, which are both rewritable and non-volatile, and which are now available with relatively very large memory capacities.

The recorder then comprises a case provided on one side with an opening through which the removable memory card can be inserted. Once the recording has been completed, the card containing the data that has been sensed is extracted from the case and is handed over to the practitioner or is sent to a remote center for analyzing the data contained therein for diagnostic purposes.

The use of a reprogrammable microcontroller presents the advantage of enabling the instrument to be upgraded without requiring any component changes, nor even changes of the instrument as a whole. Reprogramming the microcontroller can be used to correct possible defects in the program and/or to add new functions to existing instruments by means of new versions of the program, thus making it possible to satisfy clients who are very sensitive to progress.

In general, reprogramming the microcontroller requires a specific connection to be made to the microcontroller, as defined by the manufacturer of the component, and usually comprising a serial link and a plurality of associated control lines. The printed circuit carrying the microcontroller carries some number of contacts for reprogramming purposes, and these must be accessible from the outside without dismantling the instrument, e.g., via an opening formed in the case in register with the reprogramming contacts, which opening must be capable of being closed off permanently except while reprogramming is taking place by means of a suitable closure member.

Since the recorder is carried by the patient under a wide variety of circumstances and over a long duration, it can be subjected to an environment that is wet, dusty, etc., and it is essential to protect the removable memory and the circuit inside the case effectively therefrom. The environment in which the instrument is to be found can also present disturbances in the form of parasitic electrical fields and the risk of electrostatic discharges. Access to the card connector, and also to any other opening in the case (in particular the opening giving access to the reprogramming contacts), thereby needs to be protected against this type of attack from the outside environment.

In order to perform reprogramming, the opening giving access to the reprogramming contacts is uncovered so as to give access to these various contacts. These contacts then have signals applied thereto serving to force the microcontroller to take on a reprogramming mode, and then various special combinations of signals are applied to the control lines in a predetermined sequence enabling the microcontroller to be controlled in desired manner.

These specific connections require a relatively large number of contacts and control lines leading to the microcontroller, and that complicates the design of the instrument, which it is desired to make as small as possible with as few as possible external openings in order to better satisfy the general requirements of portable instruments.

OBJECTS AND SUMMARY OF THE INVENTION

One of the objects of the invention is to propose a special configuration of a self-contained electronic instrument that makes it possible to avoid having any opening dedicated to accessing reprogramming contacts, and thus avoids problems associated with positioning such an opening and closing it off in sealed manner.

Another object of the invention is to make it possible to reduce the number of reprogramming lines needed for the microcontroller, thus enabling the number of reprogramming contacts to be reduced, thereby avoiding unnecessary complication in the design of the electronic circuit.

The instrument of the invention is of the general type comprising: circuitry and a set of electronic components including a microcontroller or microprocessor; a connector block defining an inside volume with a lateral orifice suitable for receiving a removable memory card, the connector block including a set of contact terminals for making contact with corresponding set of contact surfaces of the memory card; a printed circuit carrying the electronic components, the circuitry, and the connector block; a case housing the printed circuit and including, in registration with the lateral orifice of the connector block, an opening for inserting a removable memory card; and a plurality of reprogramming contacts placed on the printed circuit and suitable for enabling electrical signals for reprogramming the microcontroller to be applied to the circuitry from the outside of the instrument.

In a manner characteristic of the invention, the reprogramming contacts are disposed on the printed circuit at a distance from said contact terminals for making contact with the memory card, in the space occupied by the connector block on the printed circuit, and opening out into the inside volume of the connector block.

In particular, the instrument can thus be essentially free of any opening dedicated to accessing the reprogramming contacts, with access to said contacts being possible via said opening from said inside volume of the connector block, said volume being empty of any memory card inserted in the instrument.

Advantageously, the instrument further comprises an interface circuit between firstly the reprogramming contacts and secondly lines connected to predetermined pins of the microcontroller, the number of lines being greater than the number of reprogramming contacts.

It is thus possible to reduce the number of reprogramming contacts, e.g., to four contacts (with a ground contact, two serial inlet/outlet contacts, and a contact for controlling the presence of reprogramming)—or even to three contacts (with a ground contact and two serial inlet/outlet contacts), but at the cost of making the electronics more complicated.

It is also possible to use certain lines of the flash card to establish the connection(s), such as the two "SPI" serial lines of the card SD which, with the help of a multiplexing system, can be used for serial transmission.

In a particular configuration, the connector block has an anterior portion carrying the terminals for contacting the memory card, and between said anterior portion and the lateral insertion orifice for receiving the memory card, a portion including at least one window formed between the inside volume of the connector block and the printed circuit, the reprogramming contacts being disposed on the printed circuit in the region of said window.

Furthermore, the reprogramming contacts are preferably contact areas formed on said printed circuit.

The present invention also provides, as a novel device, a connection cord for connection to a unit external to the above-described instrument, the cord comprising a multiconductor cable provided at one of its ends with an insert dimensioned to the format of a removable memory card so as to be capable of being inserted into the instrument via said opening instead of and replacing a memory card, said insert carrying a plurality of contact members disposed, when the insert is inserted into the instrument, in respective positions so as to come into contact with the reprogramming contacts, and/or with certain contacts for the memory card, each of said contact members being connected to a respective conductor of the cable and/or to another contact member, either directly or else via a circuit for adapting the characteristics of the signals interchanged between the external unit and the microcontroller or microprocessor.

The external instrument may be in particular a unit for reprogramming the microcontroller or microprocessor, or a unit for diagnosing and taking control of the instrument.

BRIEF DESCRIPTION OF THE DRAWINGS

An embodiment of the apparatus of the invention is described below with reference to the accompanying drawings in which the same numerical references are used from one figure to another to designate elements that are identical, and in which:

FIG. 1 is a general view of a self-contained electronic instrument to which the present invention can be applied, together with its removable memory card;

FIG. 2 is a plan view of the printed circuit of the instrument of the invention together with the various elements it supports, and a removable memory card together with a specific connection cord that is for reprogramming; and FIG. 3 is a fragmentary view in elevation and in section showing the connector block present on the circuit of FIG. 2, showing how it is possible to insert either a removable memory card, or else an insert giving access to the reprogramming contacts.

DETAILED DESCRIPTION OF THE INVENTION

In FIG. 1, reference 10 is an overall reference designating a self-contained electronic instrument, e.g., a Holter recorder of electrocardiographic data such as the Spiderview or Spiderflash brand models sold by ELA Médical, Montrouge, France.

The instrument serves to record data on a removable memory card 12 which is a standard type of flash memory, e.g., of the SD Card type. This type of card is naturally not limiting, and other card formats can be used: CompactFlash, MultiMediaCard, XD Card, etc.

The memory card 12 is for insertion in a housing 14 inside the instrument 10 through an opening 16 that can be closed off in a sealed manner by a flap 18.

As shown in FIGS. 2 and 3, the instrument 10 contains a printed circuit 20 supporting and connecting together a set of electronic components, including in particular a reprogrammable microcontroller 22. The printed circuit 20 also supports a connector block 24 suitable for receiving the memory card 12 and provided with contact terminals 26 having contact surfaces that are complementary to contact surface 28 of the memory card 12.

As can be seen more precisely in the section view of FIG. 3, the connector block 24 is in the form of a rectangular box having a top face 30, a bottom face 32 in contact with the printed circuit 20, and side faces 34, the box defining an inside volume 36 suitable for receiving the card 12. The box of the connector block is open on its side 38 so as to enable the card to be inserted therein, and on its end remote from said opening it includes mechanical means 40 for locking and for releasing the memory card, together with the contact terminals 26.

This type of connector block 24 constitutes a component that is itself well known and widely available, and it generally includes a window 42 formed in the bottom face 32 and a window 44 formed in the top face 30.

These windows 42 and 44 are situated in non-functional portions of the connector, remotely from the contact terminals 26, and they leave a region 46 of the printed circuit uncovered.

In the invention, this uncovered region 46 is used as a location for reprogramming contacts, to which access can then be obtained, after the memory card has been removed, via the opening 16 that is normally designated to receive the memory card 12.

Contact can be made with the reprogramming contacts 48 in particular by means of a connection cord 50 having an insert 52 with dimensions that match the format of a memory card (so as to enable it to be inserted in the connector block 24 and so as to enable it to be mechanically locked therein), but including contact blades 54 on its bottom face that are disposed in positions so as to come into contact with the respective reprogramming contacts 48 when the insert 52 is fully inserted into the connector block 24. Each of these blades 54 is connected to a conductor 56 of a cable 58 in the cord 50, with the other end of the cable being terminated by a plug 60 suitable for direct connection to the reprogramming unit, for example.

In certain configurations, it can be necessary to interface the microcontroller lines with the outlet of the reprogramming system in a manner that is more complex: this applies for example to a USB outlet of a microcomputer for connecting with an asynchronous or a synchronous serial link, requiring a microcontroller to be installed that is dedicated to USB management. The connection line should then be fitted with an electronic circuit serving to adapt the characteristics of the signals interchanged with the reprogramming unit and those interchanged with the microcontroller, said circuit being located either on the contact plug or at some other location.

In this way, in order to implement the electrical connections, it is possible to satisfy all of the conditions required by the connection that is specific to reprogramming, while using an opening that is dedicated to giving access to a memory card.

This takes advantage of the sealing provided by the closure flap 18, and of the protection provided against parasitic electromagnetic fields and the risks of electrostatic discharges, which protection is already provided for the removable memory card when situated inside the box.

Optimizing this configuration requires reducing the number of connection lines to the microcontroller, and thus the number of reprogramming contacts. Given the small size of the connector, it is advantageous to use as small a number of lines as possible in order to avoid pointlessly complicating assembly and remain within the confines of the windows 42 and 44 in the connector block 24.

It is thus possible in some cases to reduce the connection to four lines, comprising a ground line, two serial lines (go and return for an asynchronous link), and a presence line to force the microcontroller into reprogramming mode; a special circuit serves simply to interface this single control line to the plurality of lines of the microcontroller that are involved with reprogramming.

It should be observed that this number of four lines is not limiting. In some cases it is possible to reduce the number to three, by omitting the specific presence line and by using the two serial lines in a special configuration for transmitting commands—with this reduction involving added complexity to the associated electronics. Conversely, in a simplified configuration, it is possible to provide five lines, with two specific presence lines and/or a clock line (synchronous transmission), some of which may be shared with the contacts for the memory card itself.

While remaining within the context of the present invention, it is possible to use the teaching of the invention for applications other than reprogramming. In particular, it can be desirable to control the microcontroller on demand from the outside, in particular for diagnostic purposes or for development purposes. This technique, known as "in situ" emulation of the microcontroller, consists in using serial lines, e.g. "JTAG" lines to act on the microcontroller so as to read all of its registers in a step-by-step mode, with break points and with the majority of functions that are conventionally dedicated to an emulator. At the price of very little or even no extra complication to the interface having the above-described lines, it then becomes possible to control the instrument from the outside while its case is closed, thereby opening up a wide range of possibilities, either for testing it in a final configuration, or for reading the data that the instrument has in a memory, but that it has not been possible to extract therefrom, e.g., as a result of a malfunction.

It will be understood in this respect that the use of the term "reprogramming contacts" in the present description does not imply any restriction on the use to which such contacts can be put: the application of the invention to reprogramming a microprocessor or a microcontroller is not restricted in any way, and the invention can equally well be used in the context of other applications—such as the above-mentioned "in situ" emulation—that relates to apparatuses having a microprocessor or a microcontroller that is not necessarily reprogrammable. It also will be understood that the invention can be practiced by other than the embodiments disclosed, which are presented for purposes of illustration and not limitation.

We claim:

1. A self-contained electronic instrument comprising:
   circuitry and a set of electronic components including a microcontroller or microprocessor;
   a connector block defining an inside volume suitable for receiving a removable memory card having therein a first set of contact terminals, the connector block having a second set of contact terminals for correspondingly making contact with the first set of contact terminals of the removable memory card;
   a printed circuit carrying the set of electronic components, the circuitry, and the connector block;
   a case housing the printed circuit and including, in registration with a lateral orifice of the connector block, a first opening through which the removable memory card is receivable; and
   a plurality of reprogramming contacts for reprogramming the microcontroller or microprocessor from a programming device outside of the instrument;
   wherein the plurality of reprogramming contacts are disposed on the printed circuit at a distance from the second set of contact terminals for making contact with the first set of contact terminals of the memory card, in a space occupied by the connector block,
   wherein the plurality of reprogramming contacts are accessible via a second opening from the inside volume of the connector block, and
   wherein the microcontroller or microprocessor is reprogrammed from the programming device using an insert having a plurality of contact blades, and when the insert is inserted for programming the microcontroller or microprocessor into the connector block, the plurality of contact blades of the insert extend through the second opening and make contact with the plurality of reprogramming contacts.

2. The instrument of claim 1, in which the instrument is essentially lacking in any opening dedicated to accessing the plurality of reprogramming contacts, said inside volume being empty of any memory card inserted in the instrument.

3. The instrument of claim 1, in which the instrument is an ambulatory medical recorder.

4. The instrument of claim 1, wherein the microprocessor or microcontroller comprises a set of predetermined pins, further comprising an interface circuit between said plurality of reprogramming contacts and lines connected to said set of predetermined pins, the number of the lines being greater than the number of the plurality of reprogramming contacts.

5. The instrument of claim 4, wherein said plurality of reprogramming contacts further comprise at least three reprogramming contacts, a ground contact, and two serial inlet/outlet contacts.

6. The instrument of claim 5, wherein said plurality of reprogramming contacts further comprise a presence contact to force the microprocessor or microcontroller into a reprogramming mode.

7. The instrument of claim 5, wherein said plurality of reprogramming contacts further comprise JTAG contacts for externally controlling and diagnosing the instrument.

8. The instrument of claim 1, in which the connector block has an anterior portion, the second set of contact terminals for contacting the first set of contact terminals of the memory card, and between said anterior portion and the lateral orifice for receiving the memory card, a portion including at least one window formed between the inside volume of the connector block and the printed circuit, the plurality of reprogramming contacts being disposed on the printed circuit in the region of said window.

9. The instrument of claim 1, in which the plurality of reprogramming contacts further comprise contact areas formed on said printed circuit.

10. The instrument of claim 1, wherein the programming device is connected to the instrument using a connection cord.

11. The instrument of claim 10, wherein one end of the connection cord is connected to the plurality of contact blades of the insert.

12. The instrument of claim 11, wherein the other end of the connection cord is terminated by a plug for connecting to the programming device.

13. The instrument of claim 10, wherein the connection cord is a USB cable.

14. The instrument of claim 1, wherein the first opening is removably closed with a closure flap.

15. The instrument of claim 1, wherein the insert is dimensioned to the format of the removable memory card.

* * * * *